United States Patent
Aicher et al.

(10) Patent No.: US 9,308,185 B2
(45) Date of Patent: Apr. 12, 2016

(54) GLYCO-SUBSTITUTED DIHYDROXY-CHLORINS AND β-FUNCTIONALIZED CHLORINS FOR ANTI-MICROBIAL PHOTODYNAMIC THERAPY

(75) Inventors: Daniel Aicher, Berlin (DE); Volker Albrecht, Nuthetal (DE); Burkhard Gitter, Jena (DE); Christian B. W. Stark, Leipzig (DE); Arno Wiehe, Berlin (DE)

(73) Assignee: Biolitec Pharma Marketing LTD, Labuan (MY)

( * ) Notice: Subject to any disclaimer, the term of this patent is extended or adjusted under 35 U.S.C. 154(b) by 0 days.

(21) Appl. No.: 13/189,113

(22) Filed: Jul. 22, 2011

(65) Prior Publication Data

US 2012/0263625 A1   Oct. 18, 2012

Related U.S. Application Data

(60) Provisional application No. 61/366,718, filed on Jul. 22, 2010.

(51) Int. Cl.
*C07H 15/26* (2006.01)
*A61K 31/409* (2006.01)
*A61K 31/185* (2006.01)
*A61K 31/19* (2006.01)
*A61K 31/7056* (2006.01)
*A61K 41/00* (2006.01)
*A61K 47/48* (2006.01)

(52) U.S. Cl.
CPC ............... *A61K 31/185* (2013.01); *A61K 31/19* (2013.01); *A61K 31/409* (2013.01); *A61K 31/7056* (2013.01); *A61K 41/0071* (2013.01); *A61K 47/48092* (2013.01); *C07H 15/26* (2013.01)

(58) Field of Classification Search
CPC ....................................................... C07H 15/26
See application file for complete search history.

(56) References Cited

PUBLICATIONS

Wikipedia, Tetraphenylporphyrin, 2013. abstract included only.*
An et al. "Spectroscopic and molecular modeling of the binding of meso-tetrakis(4-hydroxyphenyl)porphyrin to human serum albumin".Dyes and Pigments, 81, 2009, 1-9.*
Cherian et al. Adsorption and Photoactivity of Tetra(4-carboxyphenyl)porphyrin (TCPP) on Nanoparticulate TiO2. Journal of Physical Chemistry B, 2000, 104, 3624.*

* cited by examiner

*Primary Examiner* — Brian McDowell
(74) *Attorney, Agent, or Firm* — BJ Associates; Bolesh J. Skutnik

(57) ABSTRACT

Antimicrobial molecular conjugates for the treatment and prevention of infectious diseases caused by pathogenic microorganisms in human and animals are provided. The conjugates are of the class of compounds of dihydroxychlorins or β-functionalized chlorins connected to carbohydrate moieties and having the general formula

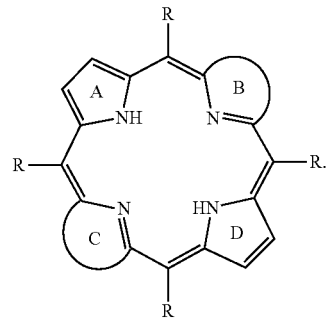

10 Claims, 4 Drawing Sheets

Figure 1

5,10,15-Tris-(3-β-D-glucosylphenyl)-20-[3,5-bis-(trifluoromethyl)-phenyl]-porphyrin

Figure 2

5,10,15-Tris-(3-β-D-glucosylphenyl)-20-[3,5-bis-(trifluoromethyl)-phenyl]-17,18-dihydroxy-17,18-chlorin 5,10,15-Tris-(3-β-D-lactosylphenyl)-20-[3,5-bis-(trifluoromethyl)-phenyl]-17,18-dihydroxy-17,18-chlorin 5,10,15,20-Tetrakis-(3-β-D-glucosylphenyl)-7,8-dihydroxy-7,8-chlorin

GLYCO-SUBSTITUTED DIHYDROXY-CHLORINS AND β-FUNCTIONALIZED CHLORINS FOR ANTI-MICROBIAL PHOTODYNAMIC THERAPY

DOMESTIC PRIORITY UNDER 35 USC 119(E)

This application claims the benefit and priority of U.S. Provisional Application Ser. No. 61/366,718 filed on Jul. 22, 2010, entitled "Glyco-substituted Dihydroxy-Chlorins and beta-functionalized Chlorins for Anti-Microbial Photodynamic Therapy" by Daniel Aicher, Volker Albrecht, Burkhard Gitter, Christian B. W. Stark and Arno Wiehe, which is incorporated by reference herein.

BACKGROUND OF THE INVENTION

1. Field of the Invention

The invention relates generally to photodynamic therapy and more particularly, to the use of glyco-substituted dihydroxychlorins or glyco-substituted β-functionalized chlorin derivatives as photosensitizers for the treatment and prevention of microbial infectious diseases in human and animals.

2. State of the Art

Photodynamic therapy (PDT) is one of the most promising new techniques now being explored for use in a variety of medical applications, and particularly is a well-recognized treatment for the destruction of tumors. Photodynamic therapy uses light and a photosensitizer (a dye) to achieve its desired medical effect.

Antimicrobial photodynamic therapy is a very promising, relatively new method for combating bacterial infections even for resistant strains. Fortunately, no resistance to photodynamic destruction has been reported to be acquired by bacteria nor is it likely since the "killing species" is oxygen. Bacterial cells treated with photosensitizers were shown to be successfully killed by photo illumination. Due to the obvious differences between bacteria and malignant cells, photosensitizers with a different mode of action were needed for an antimicrobial PDT.

Effectiveness of the photosensitizers depends strongly on the bacterial cell wall as it becomes the limiting factor for the sensitizer penetration. While Gram-positive cells could be killed sufficiently by PDT, Gram-negative cells are more resistant to killing.

A major problem for the use of anti-microbial PDT is a blocking action of the components of the blood whose presence decreases the activity of photosensitizers. A high bactericidal photodynamic activity in PBS buffer could be decreased remarkably when blood serum or blood is added.

One of the prospective approaches to increase the specificity of photosensitizers and the effectiveness of PDT against bacterial infection is to conjugate a photosensitizer with a ligand-vector, which specifically binds to receptors on the surface of a target cell. In the prior art different methods have been used to effectively target the pathogen or infected cells.

U.S. Pat. No. 6,977,075 by Hasan et al. discloses a method of killing intracellular pathogens using antibiotics and PDT. The intracellular pathogens are targeted using conjugated photosensitizers. Targeting moiety used are molecules or a macromolecular structure that target macrophages or that interacts with a pathogen. Effectiveness of the conjugate against Gram-negative bacteria, and, in complex environment is not disclosed.

U.S. Pat. No. 6,573,258 by Bommer et al. describes cationic porphyrins which can effectively target both Gram-positive and Gram-negative bacteria when present at much lower concentrations and at much shorter irradiation times. The novel porphyrins have one hydrophobic tail consisting of at least one hydrocarbon chain of between 6 and 22 carbon in length. Bacterial targeting depends upon the carbon chain length and is not very effective.

U.S. Pat. No. 6,462,070 by Hasan et al. discloses a photosensitizer conjugated to polylysine which is linked to a histatin targeting moiety to treat disorder of the oral cavity infected by microorganism. These materials have trouble working in the presence of body fluids, such as saliva, blood, etc.

U.S. Pat. No. 5,466,681 describes a variety of conjugates useful for the treatment of infectious diseases due to pathogenic microorganisms. The conjugates comprise at least one agent coupled to a microorganism receptor—a carbohydrate vector, which is able to bind selectively to a microorganism. This patent discloses a conjugate comprising at least one agent that is an anti-infective, which couples to a microorganism receptor. Agents such as antibiotics, synthetic drugs and steroids are mentioned. Since photosensitizers do not themselves interact with microbes, they are not considered agents as described in this patent and were not disclosed therein.

Other promising approaches are about conjugates of porphyrins and carbohydrates. The publication: "Nitroglycosylated meso-arylporphyrins as Photoinhibitors of Gram positive Bacteria", V. Sol, P. Branland, R. Granet, C. Kaldapa, B. Verneuil, P. Krausz, *Bioorg. Med. Chem. Lett.* 1998, 8, 3007-3010 describes the photodynamic activity of glycosylated nitroaryl-substituted porphyrins against Gram-positive bacteria, but no efficacy against Gram-negative bacteria and efficacy in complex environment is described. Moreover, the conjugates only show photodynamic activity when nitro-groups are present in the molecules.

Chlorins, as referred to in the present invention, are porphyrin derivatives, in which one double bond of the aromatic system in β-position is absent. Many current photosensitizers are not efficient enough as they have low absorption in the red region of the spectrum. Chlorins have the advantage that they possess an intense absorption in the red and near-infrared region of the electromagnetic spectrum which allows a deeper penetration of the light into the tissue. U.S. Pat. No. 7,022,843B1 by MacAlpine et discloses a variety of β,β'-dihydroxy meso-substituted chlorins as photosensitizers but do not offer guidance for treatment of microbial infectious diseases. Conversely, International Publication No. WO 2010/033678 by Wiehe et al. disclose unsymmetrically meso-substituted porphyrins and chlorins for diagnostic and PDT applications, including viral or infection diseases, however their effectiveness for both Gram-positive and Gram-negative bacteria in complex medium is not clearly conveyed.

There remains an urgent requirement to develop molecular conjugates which can actively target both Gram-positive and Gram-negative bacteria. Also they need to work under in vivo conditions, where typically blood and other body fluids are present, to use with patients directly to help protect them from deleterious microorganisms.

OBJECTIVES AND BRIEF SUMMARY OF THE INVENTION

It is an objective of the present invention to provide biologically active conjugates for targeting pathogenic microorganism causing infectious diseases.

It is another objective of the present invention to develop a photodynamic method for inactivation/reduction of bacteria (both Gram-positive and Gram-negative) in complex environment like blood, serum and saliva.

It is yet another objective of the present invention to use dihydroxychlorin-glyco-conjugates for applications in antimicrobial photodynamic therapy.

It is still another objective of the present invention to use chemically stable conjugates of β-functionalized chlorin derivatives and carbohydrates for an application in anti-microbial photodynamic therapy.

It is a further objective of the present invention to provide a method to prepare and purify glyco-substituted chlorin derivatives.

Briefly stated, the present invention provides antimicrobial molecular conjugates for the treatment and prevention of infectious diseases caused by pathogenic microorganisms in human and animals. The key to these conjugates is connecting dihydroxychlorins and β-functionalized chlorins to carbohydrate moieties. The present invention effectively works to combat infections caused by Gram-positive and Gram-negative bacteria, including their resistant strains. Significantly, they are also effective in complex environments, including blood, serum and other body fluids which are present in patient's body. A method of use to control pathogenic microorganisms in human and animals is also provided.

The above and other objects, features and advantages of the present invention will become apparent from the following description read in conjunction with the accompanying drawings.

BRIEF DESCRIPTION OF FIGURES

FIG. 1.—shows one embodiment of photodynamic inactivation using 5,10,15-tris-(3-β-glucosylphenyl)-20-[3,5-bis-(trifluoromethyl)-phenyl]-porphyrin FIG. 2.—shows one embodiment of photodynamic inactivation using 5,10,15-tris-(3-β-D-glucosylphenyl)-20-[3,5-bis-(trifluoromethyl)-phenyl]-17,18-dihydroxy-17,18-chlorin.

DETAILED DESCRIPTION OF PREFERRED EMBODIMENTS

Figure 3:
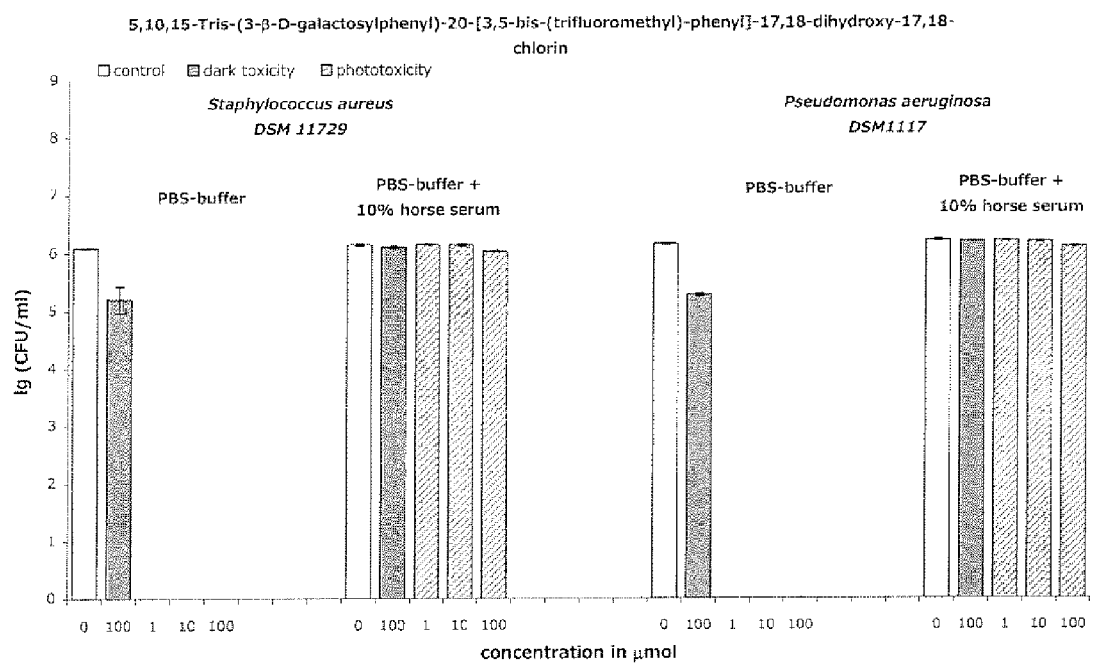
FIG. 3.—shows one embodiment of photodynamic inactivation using 5,10,15-tris-(3-β-D-galactosylphenyl)-20-[3,5-bis-(trifluoromethyl)-phenyl]-17,18-dihydroxy-17,18-chlorin.

In the present invention a photodynamic method for inactivation/reduction of bacteria in a complex environment is disclosed. Successfully combating bacterial infection in complex media present in vivo, like serum plasma or blood has shown to be one of the most difficult goals as seen in the prior art. Herein, antimicrobial photodynamic therapy is used to target pathogenic microorganisms using conjugated photosensitizers to treat various infectious diseases and also to induce photo-destruction in the complex media normally found in vivo for real patients. One of the main advantages of the molecular conjugates disclosed herein is their ability to target both Gram-positive and Gram-negative bacteria, including their resistant strains. The molecular conjugates comprise photosensitizers connected to carbohydrate moieties. It has unexpectedly been found that the presence of dihydroxychlorins and β-functionalized chlorin derivatives play a critical influence on conjugate activity. As shown in FIG. 1, a conjugate of a porphyrin and carbohydrate moieties shows a significant photodynamic inactivation of bacteria, only, in high concentrations.

The conjugates of carbohydrates disclosed herein are used to improve the specificity for microorganisms. The selectivity of the conjugate's targeting moiety allows an increased targeting effect of the photosensitizer, minimizing the dosage and potential adverse side-effects.

Furthermore, the conjugated photosensitizers of present invention enhance the effectiveness of prior art biologically active compounds, offering a deeper penetration due to their higher absorption at long wavelength of the red and near-infrared region of the electromagnetic spectrum.

Additionally, the conjugates provided by the present invention have the advantage that they are easily produced. Starting from chemically stable porphyrin or β-functionalized-chlorin derivatives, the glycosylation can be achieved by using trichloroacetimidates as glycosyl donors.

In a preferred embodiment, a carbohydrate and dihydroxychlorin conjugate compound for eliminating/reducing/destroying pathogenic microorganisms in complex environments of real patients has the general formula:

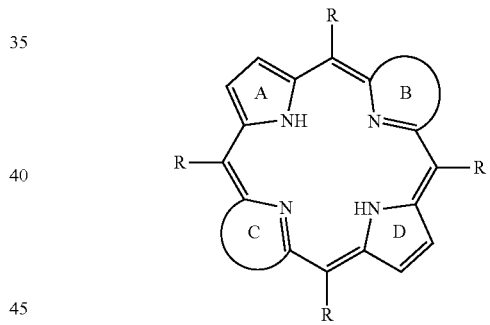

wherein B and C are selected from:

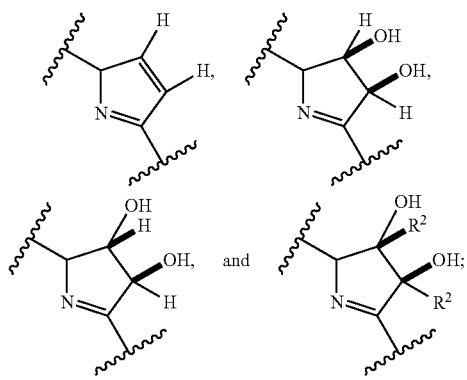

and R is a substituent comprising one or more carbohydrate groups.

In another embodiment, a conjugate of a carbohydrate and a dihydroxychlorin for eliminating microorganisms is based on the formulas 1 or 2:

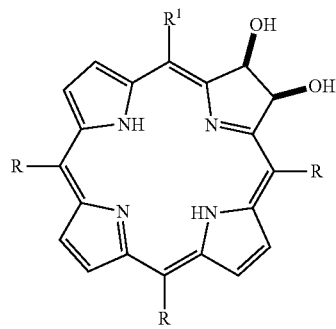

1

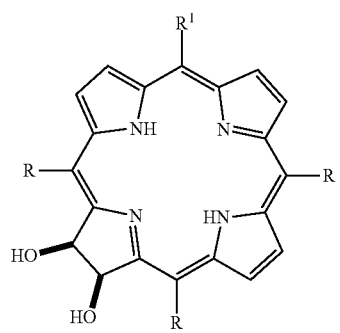

2

In this embodiment, R is a substituent comprising one or more carbohydrate groups; $R^1$ is a substituted or unsubstituted alkyl or fluoroalkyl group consisting of 1-15 carbon atoms, a phenyl ring, or a phenyl ring with one or more substituent X in the ortho-, meta- or para-position of the phenyl ring. The substituent X is OH, —COOH, —NH$_2$, —CF$_3$, —F, —COOY, —NHY, —OY, —NH—Z—COOH, and —CO—Z—NH$_2$, the substituent Y is a polyethylene glycol residue containing a (CH$_2$CH$_2$O)$_n$ moiety with n=1-30, and the substituent Z are peptides or oligopeptides.

In another embodiment, a conjugate of a carbohydrate and a dihydroxychlorin for eliminating microorganisms is based on the formula 3:

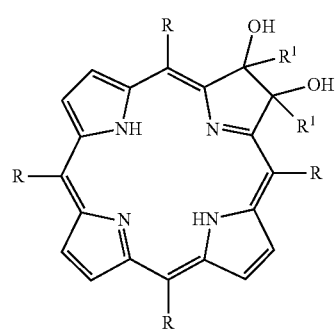

3

In this formula, R is a substituent comprising one or more carbohydrate groups; $R^1$ is a substituted or unsubstituted alkyl, alkenyl, alkynyl or fluoroalkyl group consisting of 1-15 carbon atoms, a phenyl ring, or a phenyl ring with one or more substituent X. The substituent X of the phenyl ring is either in the ortho-, meta- or para-position of the phenyl ring and is OH, —COOH, —NH$_2$, —CF$_3$, —F, —COOY, —NHY, —OY, —NH—Z—COOH, or —CO—Z—NH$_2$. The substituent Y is a polyethylene glycol residue containing a (CH$_2$CH$_2$O)$_n$ moiety with n=1-30 or a carbohydrate moiety; and Z are peptides or oligopeptides. Alternatively, in order to have a carbohydrate and a β-functionalized chlorin for eliminating pathogenic microorganisms based on formula 3, $R^1$ is a substituted or unsubstituted alkyl, alkenyl, alkynyl, or fluoroalkyl group consisting of 1-15 carbon atoms, or a phenyl ring substituted with one or more CF$_3$-groups either in the ortho-, meta- or para-position of the phenyl ring.

In another embodiment, the carbohydrate and a dihydroxychlorin conjugate compound for eliminating pathogenic microorganisms is based on the formulas 4 or 5:

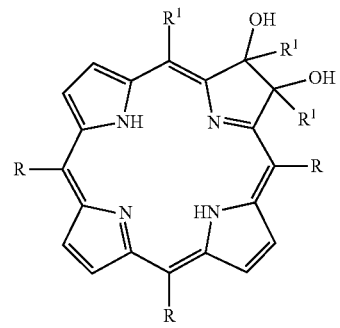

4

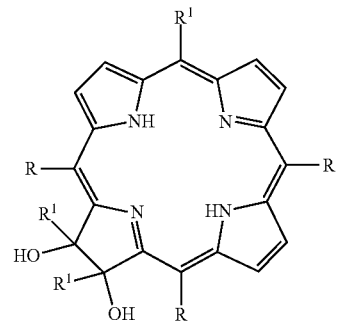

5

In this example, R is a substituent comprising one or more carbohydrate groups; $R^1$ is a substituted or unsubstituted alkyl, alkenyl, alkynyl, or fluoroalkyl group consisting of 1-15 carbon atoms, a phenyl ring, or a phenyl ring with one or more substituents X either in the ortho-, meta- or para-position of the phenyl ring The substituent X is OH, —COOH, —NH$_2$, —CF$_3$, —F, —COOY, —NHY, —OY, —NH—Z—COOH, or —CO—Z—NH$_2$, Y is a polyethylene glycol residue containing a (CH$_2$CH$_2$O)$_n$ moiety with n=1-30, and Z are peptides or oligopeptides.

In another embodiment, a conjugate compound for destroying, eliminating, and/or reducing pathogenic microorganisms in complex environments is based on the formulas 1 or 2; wherein R is a substituent comprising one or more carbohydrate groups; $R^1$ is a substituted or unsubstituted alkyl or fluoroalkyl group consisting of 4-15 carbon atoms, or a phenyl ring with one or more substituents X either in the meta- or para-position of the phenyl ring. The substituent X is OH, —COOH, —NH$_2$, or —CF$_3$.

In another embodiment, the conjugate compound is based on the formulas 4 or 5:

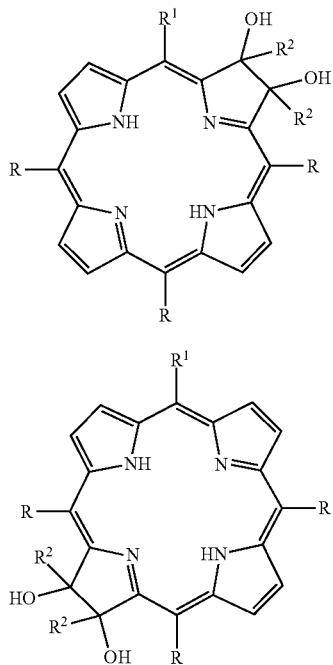

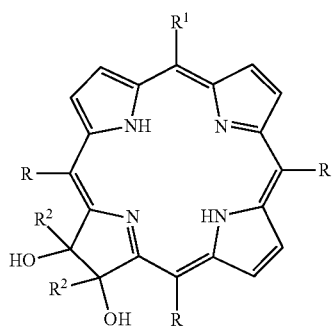

R is a substituent comprising one or more carbohydrate groups; $R^1$ is s a substituted or unsubstituted alkyl or fluoroalkyl group consisting of 4-15 carbon atoms, or a phenyl ring with one or more substituent X in the meta- or para-position of the phenyl ring. The substituent X is OH, —COOH, —NH$_2$, or —CF$_3$. And $R^2$ is a substituted or unsubstituted alkyl, alkenyl, a alkynyl, or fluoroalkyl group consisting of 1-15 carbon atoms, or a phenyl ring substituted with one or more CF$_3$-groups either in the ortho-, meta- or para-position.

In another embodiment, a compound for eliminating/reducing microorganisms is based on the formula 1:

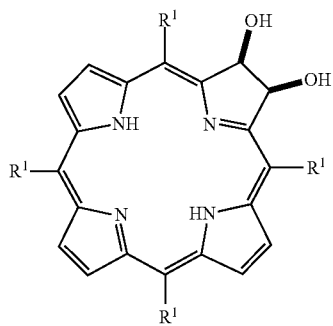

In the formula, $R^1$ is a phenyl ring with a substituent X either in the meta- or para-position, and is a glucosyl, galactosyl, mannosyl, 2-acetamidoglucosyl, lactosyl, cellobiosyl, maltosyl or 3,4,6-trideoxy-3-(dimethylamino)-D-xylo-hexopyranosyl substituent.

In another embodiment, a compound for eliminating/reducing microorganisms is based on the formulas 1 or 2:

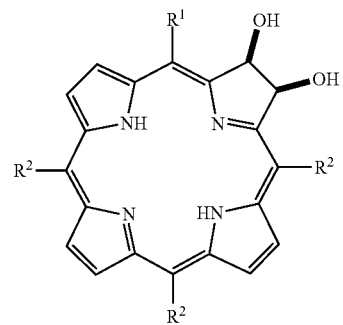

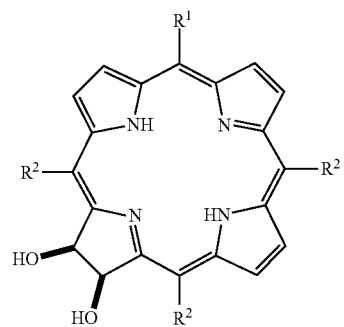

In the formulas, $R^1$ is a substituted or unsubstituted alkyl or fluoroalkyl group consisting of 4-15 carbon atoms, or a phenyl ring with one or more substituent X either in the meta- or para-position. The substituent X is selected from the group consisting of OH, —COOH, —NH$_2$, and —CF$_3$. $R^2$ is a phenyl ring with a substituent Y either in the meta- or para-position, and is a glucosyl, galactosyl, mannosyl, 2-acetamidoglucosyl, lactosyl, cellobiosyl, maltosyl or 3,4,6-trideoxy-3-(dimethylamino)-D-xylo-hexopyranosyl substituent.

In another embodiment, a carbohydrate and a β-functionalized chlorin compound is based on the formula 1:

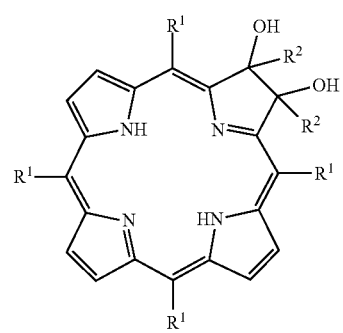

Here, $R^1$ is a phenyl ring with a substituent X either in the meta- or para-position, and is a glucosyl, galactosyl, mannosyl, 2-acetamidoglucosyl, lactosyl, cellobiosyl, maltosyl or 3,4,6-trideoxy-3-(dimethylamino)-D-xylo-hexopyranosyl substituent. $R^2$ is a substituted or unsubstituted alkyl, alkenyl, alkynyl or fluoroalkyl group consisting of 1-15 carbon atoms, or a phenyl ring substituted with one or more CF$_3$-groups either in the ortho-, meta- or para-position.

In another embodiment, a conjugate compound for eliminating/destroying/reducing pathogenic microorganisms is based on the formulas 1 or 2:

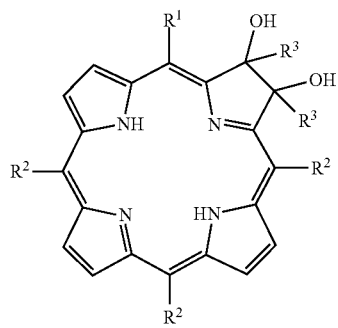

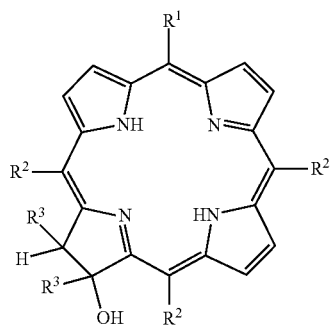

Wherein $R^1$ is a substituted or unsubstituted alkyl or fluoroalkyl group consisting of 4-15 carbon atoms, or a phenyl ring with one or more substituent X either in the meta- or para-position; and $R^2$ is a phenyl ring with a substituent Y either in the meta- or para-position. The substituent Y is a glucosyl, galactosyl, mannosyl, 2-acetamidoglucosyl, lactosyl, cellobiosyl, maltosyl or 3,4,6-trideoxy-3-(dimethylamino)-D-xylo-hexopyranosyl substituent. And $R^3$ is a substituted or unsubstituted alkyl, alkenyl, alkynyl or fluoroalkyl group consisting of 1-15 carbon atoms, or a phenyl ring substituted with one or more $CF_3$-groups either in the ortho-, meta- or para-position.

In a preferred embodiment, a photodynamic method for inactivation/reduction/elimination of pathogenic microorganisms, including Gram-positive and Gram-negative bacteria, in real patient complex environments like blood, serum and saliva, comprises the steps of selecting a molecular conjugate, selected from the previously described conjugate compounds, with a vector component targeting the microorganisms to be eliminated; introducing or administrating the vectored molecular conjugate to an environment containing pathogenic microorganisms; allowing time for the vectored conjugate to accumulate in the targeted microorganisms or contaminated environment; and irradiating the treatment site with an appropriate wavelength to activate the molecular conjugate and destroy the pathogenic microorganisms. The incubation time varies depending on many factors. In the experiments described here as an example of a photodynamic method for inactivation/reduction/elimination of microorganisms, the contaminated medium is incubated for 90 min before being irradiated with 652 nm laser at 100 $J/cm^2$ to initiate photo-destruction of bacterial cells. The conjugated photosensitizer can be administered either by systemic application, or local injection in the affected area. Alternatively, for infections on or near the skin, the conjugated photosensitizer can be administered topically.

The following examples are presented to provide those of ordinary skill in the art with an illustrative disclosure and description of how to make the dihydroxychlorin and β-functionalized chlorin derivatives of the invention and show their antimicrobial photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

EXAMPLES

All reagents were used as purchased from commercial suppliers. Dichloromethane was purified by distillation over $K_2CO_3$ prior to use. Thin layer chromatography (TLC) was performed using Merck silica gel 60 (without fluorescence indicator) pre-coated on aluminum sheets. Flash chromatography was carried out using Fluka silica gel 60, 0.040-0.063 mm (230-400 mesh). $^1H$ and $^{13}C$ NMR spectra were recorded in $CDCl_3$, $(CD_3)_2CO$, $CD_3OD$ or $(CD_3)_2SO$ on Bruker AC 250, AC 500, ECX 400, AMX 500 or AV 700 MHz instruments. Chemical shifts δ are given in ppm relative to TMS as internal standard or relative to the resonance of the residual solvent peak, J values are given in Hz. Mass spectra were recorded on Varian MAT 771, Varian IonSpee QFT-7 or Agilent 6210 ESI-TOF instrument. Electronic absorption spectra were recorded on a Specord S300 (Analytik Jena) spectrophotometer using dichloromethane, acetone or ethanol as solvent.

Example 1

Preparation of Glycosubstituted Porphyrins 1.1 Preparation of 5,10,15-tris-[3-(2,3,4,6-tetraacetyl-β-D-glucosyl)-phenyl]-20-[3,5-bis-(trifluoromethyl)-phenyl]-porphyrin In a typical experiment, under argon atmosphere, Zn(II)-5,10,15-tris-(3-hydroxyphenyl)-20-[3,5-bis-(trifluoromethyl)-phenyl]-porphyrin (300 mg, 0.35 mmol) was dissolved in 40 ml dry dichloromethane. Then, 2,3,4,6-tetraacetyl-D-glucose trichloroacetimidate (1.5 g, 3 mmol) and $BF_3 \cdot Et_2O$ (10 µl, 0.08 mmol) were added. After stirring for 1 hour, the mixture was transferred to a separatory funnel. The organic layer was washed with water (2×50 ml) and the solvent was evaporated under reduced pressure. To remove the zinc, the residue was dissolved in 40 ml THF, and 3 ml of hydrochloric acid (25%) were added. After stirring for 10 minutes, water (50 ml) and dichloromethane (75 ml) were added. The organic layer was separated and washed with water (2×50 ml). After drying with $Na_2SO_4$, the solvent was evaporated under reduced pressure. Further purification was achieved by flash chromatography, using dichloromethane/methanol 95:5 as the eluent. The analytically pure product (560 mg, 90%) was obtained as a violet crystalline solid after recrystallization from dichloromethane/aqueous methanol.

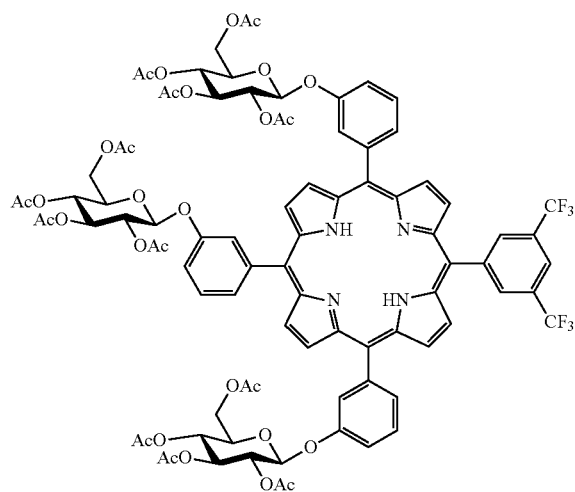

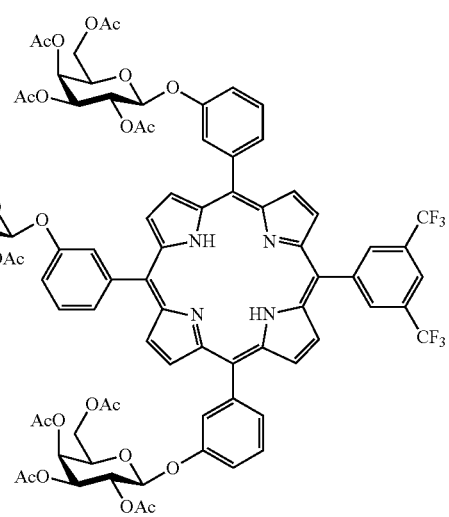

mp: 215° C.; $^1$H-NMR (500 MHz, CDCl$_3$): δ=−2.89 (s, 2 H, NH), 1.34-1.54 (m, 9H, 3×OAc), 1.98-2.09 (m, 27 H, 9×OAc), 3.76-3.88 (m, 3 H, H'ose'), 4.01-4.10 (m, 3 H, H'ose'), 4.13-4.22 (m, 3 H, H'ose'), 5.14-5.21 (m, 3 H, H'ose'), 5.29-5.40 (m, 9 H, H'ose'), 7.43-7.46 (m, 3 H, Ar), 7.66-7.72 (m, 3 H, Ar), 7.84-7.97 (m, 6 H, Ar), 8.35 (br s, 1 H, Ar), 8.65-8.72, 8.88-8.95 (2 m, 10 H, 8×β-H, 2×Ar) ppm; HRMS (ESI): $C_{88}H_{82}F_6N_4O_{30}Na^+$ ([M+Na]$^+$): required: 1811.4810; found.: 1811.4796; UV/Vis (CH$_2$Cl$_2$): $\lambda_{max}$/nm (ε/dm$^3$ mol$^{-1}$ cm$^{-1}$): 419 (196100), 514 (18900), 589 (5500), 645 (2500).

mp: 180° C.; $^1$H-NMR (500 MHz, CDCl$_3$): δ=−2.87 (s, 2 H, NH), 1.25-1.43 (m, 9 H, 3×OAc), 2.00-2.16 (m, 27 H, 9×OAc), 3.97-4.17 (m, 9 H, H'ose'), 5.11-5.16 (m, 3 H, H'ose'), 5.29-5.36 (m, 3 H, H'ose'), 5.40-5.44 (m, 3 H, H'ose'), 5.57-5.62 (m, 3 H, H'ose'), 7.41-7.43 (m, 3 H, Ar), 7.66-7.72 (m, 3 H, Ar), 7.85-7.97 (m, 6 H, Ar), 8.35 (br s, 1 H, Ar), 8.65-8.71, 8.88-8.95 (2 m, 10 H, 8×β-H, 2×Ar) ppm; HRMS (ESI): $C_{88}H_{83}F_6N_4O_{30}^+$ ([M+H]$^+$): required: 1789.4991; found: 1789.5020; UV/Vis (CH$_2$Cl$_2$): $\lambda_{max}$/nm (ε/dm$^3$ mol$^{-1}$ cm$^{-1}$): 418 (179800), 514 (18100), 548 (5900), 589 (5400), 645 (2300).

1.2 Preparation of 5,10,15-tris-[3-(2,3,4,6-tetraacetyl-β-D-galactosyl)-phenyl]-20-[3,5-bis-(trifluoromethyl)-phenyl]-porphyrin In a typical experiment, under argon atmosphere, Zn(II)-5,10,15-tris-(3-hydroxyphenyl)-20-[3,5-bis-(trifluoromethyl)-phenyl]-porphyrin (245 mg, 0.28 mmol) was dissolved in 40 ml dry dichloromethane. Then, 2,3,4,6-tetraacetyl-D-galactose trichloroacetimidate (2.5 g, 5 mmol) and BF$_3$.Et$_2$O (10 μl, 0.08 mmol) were added. After stirring for 2 days, the mixture was transferred to a separatory funnel. The organic layer was washed with water (2×50 ml) and the solvent was evaporated under reduced pressure. In order to remove the zinc, the residue was dissolved in 40 ml THF, and 3 ml of hydrochloric acid (25%) were added. After stirring for 10 minutes, water (50 ml) and dichloromethane (75 ml) were added. The organic layer was separated and washed with water (2×50 ml). After drying with Na$_2$SO$_4$, the solvent was evaporated under reduced pressure. Further purification was achieved by flash chromatography, using dichloromethane/methanol 95:5 as the eluent. The analytically pure product (243 mg, 48%) was obtained as a violet crystalline solid after recrystallization from dichloromethane/aqueous methanol.

1.3 Preparation of 5,10,15-tris-[3-(2,3,4,6-tetraacetyl-α-D-mannosyl)-phenyl]-20-[3,5-bis-(trifluoromethyl)-phenyl]-porphyrin In a typical experiment, under argon atmosphere, Zn(II)-5,10,15-tris-(3-hydroxyphenyl)-20-[3,5-bis-(trifluoromethyl)-phenyl]-porphyrin (300 mg, 0.35 mmol) was dissolved in 40 ml dry dichloromethane. Then, 2,3,4,6-tetraacetyl-α-D-mannose trichloroacetimidate (1.75 g, 3.55 mmol) and BF$_3$.Et$_2$O (10 μl, 0.08 mmol) were added. After stirring for 4 hours, the mixture was transferred to a separatory funnel. The organic layer was washed with water (2×50 ml) and the solvent was evaporated under reduced pressure. In order to remove the zinc, the residue was dissolved in 40 ml THF, and 1 ml of hydrochloric acid (25%) was added. After stirring for 10 minutes, water (50 ml) and dichloromethane (75 ml) were added. The organic layer was separated and washed with water (2×50 ml). After drying with Na$_2$SO$_4$, the solvent was evaporated under reduced pressure. Further purification was achieved by flash chromatography, using dichloromethane/methanol 95:5 as the eluent. The analytically pure product (472 mg, 76%) was obtained as a violet crystalline solid after recrystallization from dichloromethane/aqueous methanol.

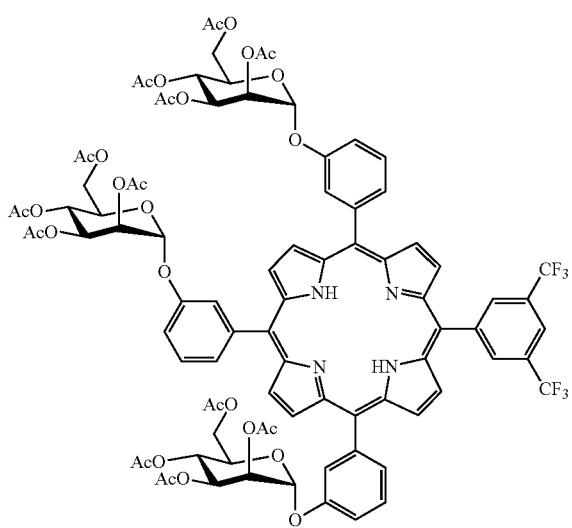

mp: 150° C.; $^1$H-NMR (500 MHz, CDCl$_3$): δ=−2.87 (s, 2 H, NH), 1.72-1.78 (m, 9 H, 3×OAc), 2.01-2.19 (m, 27 H, 9×OAc), 4.08-4.15 (m, 3 H, H'ose'), 4.26-4.35 (m, 6 H, H'ose'), 5.34-5.42 (m, 3 H, H'ose'), 5.56-5.59 (m, 3 H, H'ose'), 5.62-5.66 (m, 3 H, H'ose'), 5.79-5.82 (m, 3 H, H'ose'), 7.53-7.57 (m, 3 H, Ar), 7.67-7.72 (m, 3 H, Ar), 7.91-8.01 (m, 6 H, Ar), 8.34 (br s, 1 H, Ar), 8.67-8.71, 8.87-8.94 (2 m, 10 H, 8×β-H, 2×Ar) ppm; HRMS (ESI): C$_{88}$H$_{82}$F$_6$N$_4$O$_{30}$Na$^+$ ([M+Na]$^+$): required: 1811.4810; found: 1811.4807; UV/Vis (CH$_2$Cl$_2$): λ$_{max}$/nm (ε/dm$^3$ mol$^{-1}$ cm$^{-1}$): 418 (508300), 514 (26900), 549 (9200), 590 (8100), 646 (3800).

1.4 Preparation of 5,10,15-tris-[3-(2,3,4,6,2',3',6'-heptaacetyl-β-D-lactosyl)-phenyl]-20-[3,5-bis-(trifluoromethyl)-phenyl]-porphyrin In a typical experiment, under argon atmosphere, Zn(II)-5,10,15-tris-(3-hydroxyphenyl)-20-[3,5-bis-(trifluoromethyl)-phenyl]-porphyrin (250 mg, 0.29 mmol) was dissolved in 40 ml dry dichloromethane. Then, 2,3,4,6,2',3',6'-Heptaacetyl-α-D-lactose trichloroacetimidate (2.2 g, 2.82 mmol) and BF$_3$.Et$_2$O (10 µl, 0.08 mmol) were added. After stirring for 5 hours, the mixture was transferred to a separatory funnel. The organic layer was washed with water (2×50 ml) and the solvent was evaporated under reduced pressure. In order to remove the zinc, the residue was dissolved in 40 ml THF, and 1 ml of hydrochloric acid (25%) was added. After stirring for 10 minutes, water (50 ml) and dichloromethane (75 ml) were added. The organic layer was separated and washed with water (2×50 ml). After drying with Na$_2$SO$_4$, the solvent was evaporated under reduced pressure. Further purification was achieved by flash chromatography, using dichloromethane/methanol 95:5 as the eluent. The analytically pure product (499 mg, 66%) was obtained as a violet crystalline solid after recrystallization from dichloromethane/aqueous methanol.

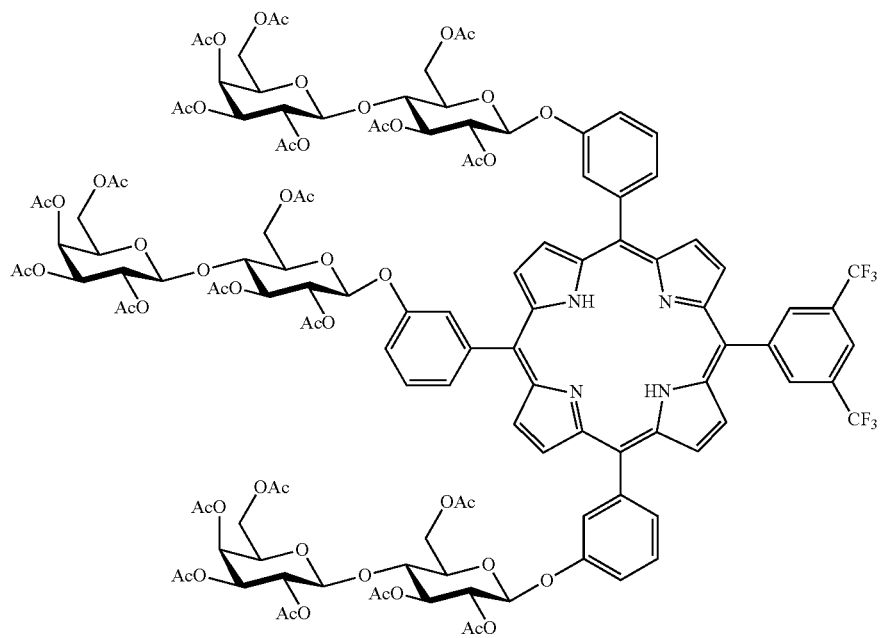

mp: 150° C.; $^1$H-NMR (400 MHz, CDCl$_3$): δ=−2.90 (s, 2 H, NH), 1.17-1.46 (m, 9 H, 3×OAc), 1.82-2.16 (m, 54 H, 18×OAc), 3.67-3.79 (m, 3 H, H'ose'), 3.82-3.93 (m, 6 H, H'ose'), 3.98-4.14 (m, 9 H, H'ose'), 4.28-4.50 (m, 6 H, H'ose'), 4.88-4.94 (m, 3 H, H'ose'), 5.02-5.08 (m, 3 H, H'ose'), 5.25-5.37 (m, 12 H, H'ose'), 7.41-7.44 (m, 3 H, Ar), 7.59-7.71 (m, 3 H, Ar), 7.80-7.96 (m, 6 H, Ar), 8.34 (br s, 1 H, Ar), 8.65-8.71, 8.87-8.94 (2 m, 10 H, 8×β-H, 2×Ar) ppm; HRMS (ESI): C$_{124}$H$_{130}$F$_6$N$_4$O$_{54}$Na$^+$ ([M+Na]$^+$): required: 2676.7385; found: 2676.7395; UV/Vis (CH$_2$Cl$_2$): λ$_{max}$/nm (ε/dm$^3$ mol$^{-1}$ cm$^{-1}$): 418 (361700), 514 (18200), 548 (5900), 590 (5600), 645 (2600).

1.5 Preparation of 5,10,15,20-tetrakis-[3-(2,3,4,6-tetraacetyl-β-D-glucosyl)-phenyl]-porphyrin In a typical experiment, under argon atmosphere, Zn(II)-5,10,15,20-tetrakis-(3-hydroxyphenyl)-porphyrin (250 mg, 0.34 mmol) was dissolved in 36 ml dry dichloromethane/acetonitrile/tetrahydrofuran 10:1:1. Then, 2,3,4,6-tetraacetyl-D-glucose trichloroacetimidate (3 g, 6 mmol) and $BF_3 \cdot Et_2O$ (15 μl, 0.12 mmol) were added. After stirring for 4 hours, the mixture was transferred to a separatory funnel. The organic layer was washed with water (2×50 ml) and the solvent was evaporated under reduced pressure. In order to remove the zinc, the residue was dissolved in 40 ml THF, and 2 ml of hydrochloric acid (25%) were added. After stirring for 10 minutes, water (50 ml) and dichloromethane (75 ml.) were added. The organic layer was separated and washed with water (2×50 ml). After drying with $Na_2SO_4$, the solvent was evaporated under reduced pressure. Further purification was achieved by flash chromatography, using dichloromethane/methanol 95:5 as the eluent. The analytically pure product (471 mg, 70%) was obtained as a violet crystalline solid after recrystallization from dichloromethane/aqueous methanol.

Example 2

Preparation of Glycosylated Deacetylated Dihydroxychlorins 2.1 Preparation of 5,10,15-tris-(3-β-D-glucosylphenyl)-20-[3,5-bis-(trifluoromethyl)-phenyl]-17,18-dihydroxy-17,18-chlorin In a typical experiment, osmium tetroxide (100 mg, 0.39 mmol) was added to a stirred solution of 5,10,15-tris-[3-(2,3,4,6-tetraacetyl-β-D-glucosyl)-phenyl]-20-[3,5-bis-(trifluoromethyl)-phenyl]-porphyrin (469 mg, 0.26 mmol) in dichloromethane/pyridine 1:1 (26 ml). After stirring for 30 minutes at 0° C. and additional 2 hours at room temperature, a saturated solution of sodium bisulfite in water/methanol 1:1 (25 ml) was added and the mixture was stirred for 18 h. The reaction mixture was filtered through Celite and dried over anhydrous sodium sulfate. The solvent was evaporated and the residue was purified by flash chromatography with dichloromethane/methanol 95:5 as eluent, followed by recrystallization from dichloromethane/aqueous methanol. 5,10,15-Tris-[3-(2,3,4,6-tetraacetyl-β-D-glucosyl)-phenyl]-20-[3,5-bis-(trifluoromethyl)-phenyl]-17,18-dihydroxy-17,18-chlorin (254 mg, 53%) was obtained as a violet crystalline solid after recrystallization from dichloromethane/aqueous methanol, as a regioisomeric mixture.

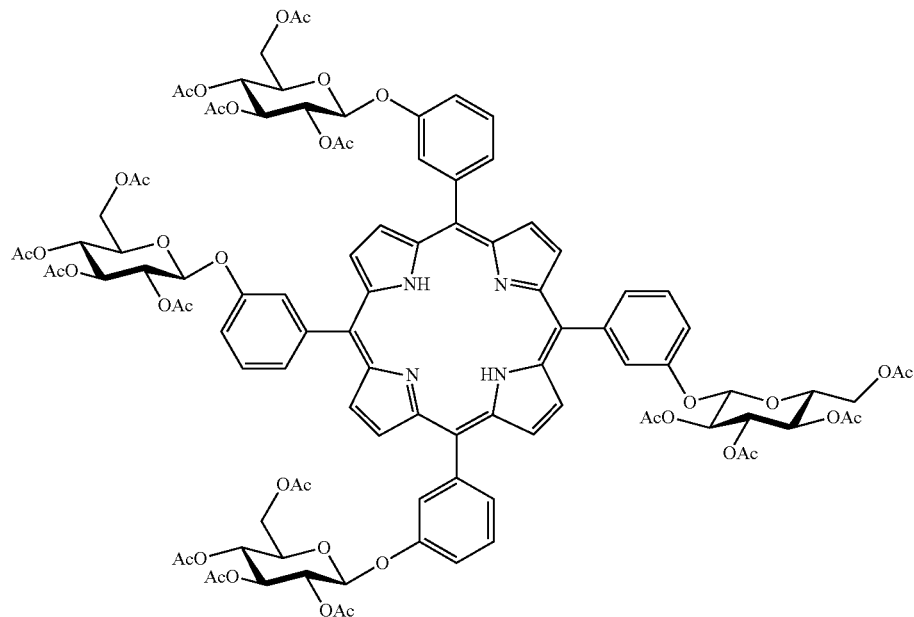

mp: 216° C.; $^1$H-NMR (400 MHz, $(CD_3)_2CO$): δ=−2.86 (s, 2 H, NH), 1.16-1.21 (m, 9 H, 3×OAc), 1.91-2.16 (m, 39 H, 13×OAc), 3.98-4.06 (m, 4 H, H'ose'), 4.09-4.15 (m, 8 H, H'ose'), 5.06-5.12 (m, 4 H, H'ose'), 5.27-5.33 (m, 4 H, H'ose'), 5.36-5.42 (m, 4 H, H'ose'), 5.74-5.79 (m, 4 H, H'ose'), 7.51-7.56 (m, 4 H, Ar), 7.73-7.79 (m, 4 H, Ar), 7.91-8.02 (m, 8 H, Ar), 8.89-8.97 (m, 8 H, β-H) ppm; HRMS (ESI): $C_{100}H_{102}N_4O_{40}Na^+$ ($[M+Na]^+$): required: 2022.5996; found: 2022.5900; UV/Vis ($CH_2Cl_2$): $\lambda_{max}$/nm (ε/dm$^3$ mol$^{-1}$ cm$^{-1}$): 418 (346600), 514 (17000), 548 (6000), 589 (5100), 645 (2700).

To a stirred solution of 5,10,15-tris-[3-(2,3,4,6-tetraacetyl-β-D-glucosyl)-phenyl]-20-[3,5-bis-(trifluoromethyl)-phenyl]-17,18-dihydroxy-17,18-chlorin (50 mg, 27 μmol) in dry tetrahydrofuran/methanol 1:1 (10 ml) under an argon atmosphere, a solution of sodium methanolate in dry methanol (1.5 ml, 0.06 N) was added. After 4 h, the solvent was evaporated under reduced pressure and the crude product was purified by flash chromatography using $RP_{18}$ silica gel and methanol/water 85:15 as the eluent. The title product (28 mg, 94%) was obtained as a violet crystalline solid after washing with dichloromethane.

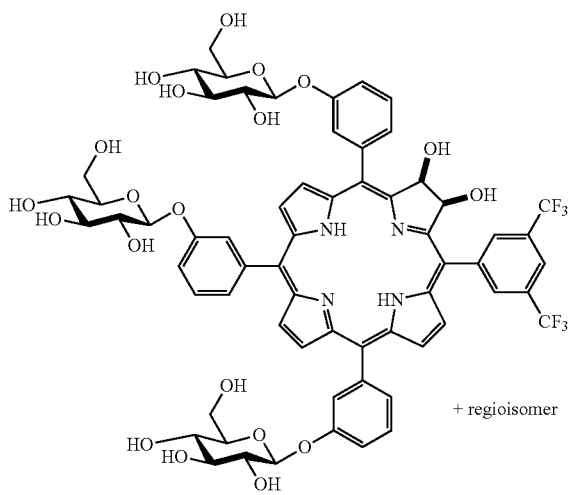

+ regioisomer mp: 180° C. $^1$H-NMR (400 MHz, CD$_3$OD): δ=3.34-3.87 (m, 18 H, H'ose'), 5.07-5.18 (m, 3 H, H'ose'), 6.11-6.35 (m, 2 H, β-H), 7.39-8.78 (m, 21 H, 6×β-H, 15×Ar) ppm; HRMS (ESI): C$_{64}$H$_{61}$F$_6$N$_4$O$_{20}{}^+$ ([M+H]$^+$): required: 1319.3778; found: 1319.3816; UV/Vis (EtOH): λ$_{max}$/nm (ε/dm$^3$ mol$^{-1}$ cm$^{-1}$): 406 (90900), 515 (7700), 540 (7200), 593 (3100), 646 (14800).

2.2 Preparation of 5,10,15-tris-(3-β-D-galactosylphenyl)-20-[3,5-bis-(trifluoromethyl)-phenyl]-17,18-dihydroxy-17,18-chlorin In a typical experiment, osmium tetroxide (100 mg, 0.39 mmol) was added to a stirred solution of 5,10,15-tris-[3-(2,3,4,6-tetraacetyl-β-D-galactosyl)-phenyl]-20-[3,5-bis-(trifluoromethyl)-phenyl]-porphyrin (300 mg, 0.17 mmol) in dichloromethane/pyridine 1:1 (26 ml). After stirring for 30 minutes at 0° C. and additional 2 hours at room temperature, a saturated solution of sodium bisulfite in water/methanol 1:1 (25 ml) was added and the mixture was stirred for 18 h. The reaction mixture was filtered through Celite and dried over anhydrous sodium sulfate. The solvent was evaporated and the residue was purified by flash chromatography with dichloromethane/methanol 95:5 as eluent, followed by recrystallization from dichloromethane/aqueous methanol. 5,10,15-Tris-[3-(2,3,4,6-tetraacetyl-β-D-galactosyl)-phenyl]-20-[3,5-bis-(trifluoromethyl)-phenyl]-17,18-dihydroxy-17,18-chlorin (129 mg, 42%) was obtained as a violet crystalline solid after recrystallization from dichloromethane/aqueous methanol, as a regioisomeric mixture.

To a stirred solution of 5,10,15-tris-[3-(2,3,4,6-tetraacetyl-β-D-galactosyl)-phenyl]-20-[3,5-bis-(trifluoromethyl)-phenyl]-17,18-dihydroxy-17,18-chlorin (46 mg, 25 µmol) in dry tetrahydrofuran/methanol 1:1 (10 ml) under an argon atmosphere, a solution of sodium methanolate in dry methanol (1 ml, 0.1 N) was added. After 4 h, the solvent was evaporated under reduced pressure and the crude product was purified by flash chromatography using RP$_{18}$ silica gel and methanol/water 85:15 as the eluent. The title product (33 mg, 99%) was obtained as a violet crystalline solid after washing with dichloromethane.

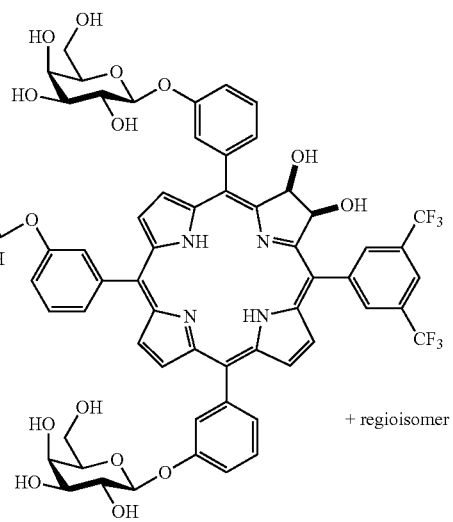

+ regioisomer mp: >300° C.; $^1$H-NMR (500 MHz, CD$_3$OD): δ=3.54-3.88 (m, 18 H, H'ose'), 5.02-5.12 (3 H, H'ose'), 6.13-6.36 (m, 2 H, β-H), 7.39-8.79 (m, 21 H, 6×β-H, 15×Ar) ppm; HRMS (ESI): C$_{64}$H$_{60}$F$_6$N$_4$O$_{20}$Na$^+$ ([M+Na]$^+$): required: 1341.3597; found: 1341.3594; UV/Vis ((CH$_3$)$_2$CO): λ$_{max}$/nm (ε/dm$^3$ mol$^{-1}$ cm$^{-1}$): 407 (32200), 515 (3400), 541 (3100), 594 (1500), 646 (6000).

2.3 Preparation of 5,10,15-tris-(3-α-D-mannosylphenyl)-20-[3,5-bis-(trifluoromethyl)-phenyl]-17,18-dihydroxy-17,18-chlorin In a typical experiment, osmium tetroxide (100 mg, 0.39 mmol) was added to a stirred solution of 5,10,15-tris-[3-(2,3,4,6-tetraacetyl-α-D-mannosyl)-phenyl]-20-[3,5-bis-(trifluoromethyl)-phenyl]-porphyrin (350 mg, 0.2 mmol) in dichloromethane/pyridine 1:1 (26 ml). After stirring for 30 minutes at 0° C. and additional 2 hours at room temperature, a saturated solution of sodium bisulfite in water/methanol 1:1 (25 ml) was added and the mixture was stirred for 18 h. The reaction mixture was filtered through Celite and dried over anhydrous sodium sulfate. The solvent was evaporated and the residue was purified by flash chromatography with dichloromethane/methanol 95:5 as eluent, followed by recrystallization from dichloromethane/aqueous methanol. 5,10,15-Tris-[3-(2,3,4,6-tetraacetyl-α-D-mannosyl)-phenyl]-20-[3,5-bis-(trifluoromethyl)-phenyl]-17,18-dihydroxy-17,18-chlorin (151 mg, 42%) was obtained as a violet crystalline solid after recrystallization from dichloromethane/aqueous methanol as a regioisomeric mixture. To a stirred solution of 5,10,15-tris-[3-(2,3,4,6-tetraacetyl-α-D-mannosyl)-phenyl]-20-[3,5-bis-(trifluoromethyl)-phenyl]-17,18-dihydroxy-17,18-chlorin (40 mg, 22 µmol) in dry tetrahydrofuran/methanol 1:1 (10 ml) under an argon atmosphere, a solution of sodium methanolate in dry methanol (1.5 ml, 0.1 N) was added. After 4 h, the solvent was evaporated under reduced pressure and the crude product was purified by flash chromatography, using RP$_{18}$ silica gel and methanol/water 85:15 as the eluent. The title

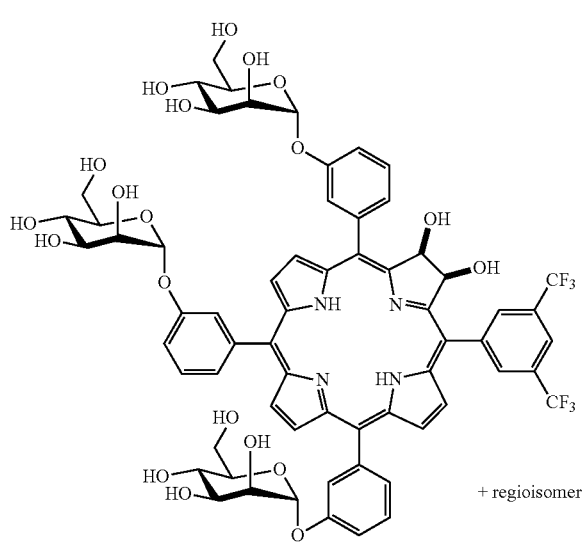

+ regioisomer product (28 mg, 97%) was obtained as a violet crystalline solid after washing with dichloromethane.

mp: >300° C.; $^1$H-NMR (400 MHz, CD$_3$OD): δ=3.65-3.89 (m, 12 H, H'ose'), 3.92-3.98 (m, 3 H, H'ose'), 4.06-4.10 (m, 3 H, H'ose'), 5.63-5.72 (m, 3 H'Hose'), 6.08-6.32 (m, 2 H, β-H), 7.38-8.79 (m, 21 H, 6×β-H, 15×Ar) ppm; HRMS (ESI): C$_{64}$H$_{60}$F$_6$N$_4$O$_{20}$Na$^+$ ([M+Na]$^+$): required: 1341.3597; found: 1341.3616; UV/Vis ((CH$_3$)$_2$CO): $\lambda_{max}$/nm (ε/dm$^3$ mol$^{-1}$ cm$^{-1}$): 415 (73100), 514 (6900), 541 (6300), 593 (2900), 646 (12100).

2.4 Preparation of 5,10,15-tris-(3-β-D-lactosylphenyl)-20-[3,5-bis-(trifluoromethyl)-phenyl]-17,18-dihydroxy-17,18-chlorin In a typical experiment, osmium tetroxide (100 mg, 0.39 mmol) was added to a stirred solution of 5,10,15-tris-[3-(2,3,4,6,2',3',6'-heptaacetyl-β-D-lactosyl)-phenyl]-20-[3,5-bis-(trifluoromethyl)-phenyl]-porphyrin (350 mg, 0.13 mmol) in dichloromethane/pyridine 1:1 (15 ml). After stirring for 30 minutes at 0° C. and additional 2 hours at room temperature, a saturated solution of sodium bisulfite in water/methanol 1:1 (25 ml) was added and the mixture was stirred for 18 h. The reaction mixture was filtered through Celite and dried over anhydrous sodium sulfate. The solvent was evaporated and the residue was purified by flash chromatography with dichloromethane/methanol 95:5 as eluent, followed by recrystallization from dichloromethane/aqueous methanol. 5,10,15-Tris-[3-(2,3,4,6,2',3',6'-heptaacetyl-β-D-lactosyl)-phenyl]-20-[3,5-bis-(trifluoromethyl)-phenyl]-7,8-dihydroxy-7,8-chlorin (39 mg, 8%) was obtained as a violet crystalline solid after recrystallization from dichloromethane/aqueous methanol, as a regioisomeric mixture.

To a stirred solution of 5,10,15-tris-[3-(2,3,4,6,2',3',6'-heptaacetyl-β-D-lactosyl)-phenyl]-20-[3,5-bis-(trifluoromethyl)-phenyl]-7,8-dihydroxy-7,8-chlorin (32 mg, 12 μmol) in dry tetrahydrofuran/methanol 1:1 (10 ml) under an argon atmosphere, a solution of sodium methanolate in dry methanol (1.5 ml, 0.1N) was added. After 4 h, the solvent was evaporated under reduced pressure and the crude product was purified by flash chromatography, using RP$_{18}$ silica gel and methanol/water 85:15 as the eluent. The title product (21 mg, 98%) was obtained as a violet crystalline solid after washing with dichloromethane.

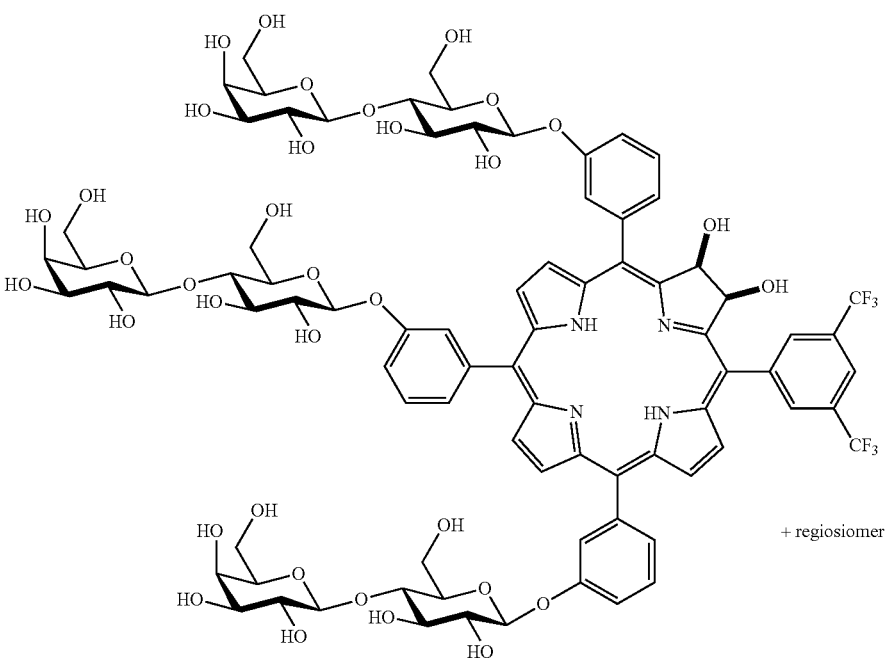

+ regioisomer mp: >300° C.; $^1$H-NMR (500 MHz, CD$_3$OD): δ=3.43-3.84 (m, 36 H, H'ose'), 4.31-4.38 (m, 3 H, H'ose'), 5.17-5.25 (m, 3 H, H'ose'), 6.13-6.32 (m, 2 H, β-H), 7.39-8.80 (m, 21 H, 6×β-H, 15×Ar) ppm; HRMS (ESI): C$_{82}$H$_{90}$F$_6$N$_4$O$_{35}$Na$^+$ ([M+Na]$^+$): required: 1827.5182; found: 1827.5282; UV/Vis (EtOH): λ$_{max}$/nm (ϵ/dm$^3$ mol$^{-1}$ cm$^{-1}$): 415 (83400), 514 (7200), 541 (6700), 594 (3100), 646 (13200).

2.5 Preparation of 5,10,15,20-tetrakis-(3-β-D-glucosylphenyl)-20-[3,5-bis-(trifluoromethyl)-phenyl]-17,18-dihydroxy-17,18-chlorin In a typical experiment, osmium tetroxide (100 mg, 0.39 mmol) was added to a stirred solution of 5,10,15,20-tetrakis-[3-(2,3,4,6-tetraacetyl-β-D-glucosyl)-phenyl]-porphyrin (455 mg, 0.23 mmol) in dichloromethane/pyridine 1:1 (26 ml). After stirring for 30 minutes at 0° C. and additional 2 hours at room temperature, a saturated solution of sodium bisulfite in water/methanol 1:1 (25 ml) was added and the mixture was stirred for 18 h. The reaction mixture was filtered through Celite and dried over anhydrous sodium sulfate. The solvent was evaporated and the residue was purified by flash chromatography with dichloromethane/methanol 95:5 as eluent, followed by recrystallization from dichloromethane/aqueous methanol. 5,10,15,20-Tetrakis-[3-(2,3,4,6-tetraacetyl-β-D-glucosyl)-phenyl]-7,8-dihydroxy-7,8-chlorin (184 mg, 40%) was obtained as a violet crystalline solid after recrystallization from dichloromethane/aqueous methanol, as a regioisomeric mixture.

To a stirred solution of 5,10,15,20-tetrakis-[3-(2,3,4,6-tetraacetyl-β-D-glucosyl)-phenyl]-7,8-dihydroxy-7,8-chlorin (40 mg, 20 μmol) in dry methanol (10 ml) under an argon atmosphere, a solution of sodium methanolate in dry methanol (1.5 ml, 0.08 N) was added. After 3 h, the solvent was evaporated under reduced pressure and the crude product was purified by flash chromatography, using RP$_{18}$ silica gel and methanol/water 85:15 as the eluent. The title product (26 mg, 97%) was obtained as a violet crystalline solid after washing with dichloromethane.

mp: 250° C.; $^1$H-NMR (400 MHz, CD$_3$OD): δ=3.36-3.57 (m, 16 H, H'ose'), 3.59-3.70 (m, 4 H, H'ose'), 3.74-3.86 (m, 4 H, H'ose'), 5.05-5.20 (m, 4 H, H'ose'), 6.18-6.43 (m, 2 H, β-H), 7.35-8.95 (m, 22 H, 6×β-H, 16×Ar) ppm; HRMS (ESI): C$_{68}$H$_{72}$N$_4$O$_{26}$Na$^+$ ([M+Na]$^+$): required: 1383.4327; found: 1383.4352; UV/Vis (EtOH): λ$_{max}$/nm (ϵ/dm$^3$ mol$^{-1}$ cm$^{-1}$): 416 (79800), 515 (5200), 543 (4200), 593 (2200), 645 (7100).

Example 3

Preparation of Glycosylated β-functionalized Chlorins 3.1 Preparation of 5,10,15,20-tetrakis-[3-(2,3,4,6-tetraacetyl-β-D-glucosyl)-phenyl]-7,8-dihydroxy-7,8-bis-(trifluoromethyl)-7,8-chlorin In a typical experiment, under argon atmosphere, Zn(II)-5,10,15,20-tetrakis-(3-hydroxyphenyl)-7,8-dihydroxy-7,8-bis-(trifluoromethyl)-7,8-chlorin (30 mg, 33 μmol) was dissolved in 10 ml dry dichloromethane/tetrahydrofuran 30:1. Then, 2,3,4,6-tetraacetyl-D-glucosetrichloracetimidat (300 mg, 0.6 mmol) and BF$_3$.Et$_2$O (4 μl, 0.04 mmol) were added. After stirring for 3 hours, the mixture was transferred to a separatory funnel. The organic layer was washed with water (2×25 ml) and the solvent was evaporated under reduced pressure. In order to remove the zinc, the residue was dissolved in 10 ml THF, and 0.3 ml of hydrochloric acid (25%) were added. After stirring for 10 minutes water (25 ml) and dichloromethane (40 ml) were added. The organic layer was separated and washed with water (2×25 ml). After drying with Na$_2$SO$_4$, the solvent was evaporated under reduced pressure. Further purification was achieved by flash chromatography using dichloromethane/methanol 95:5 as the eluent.

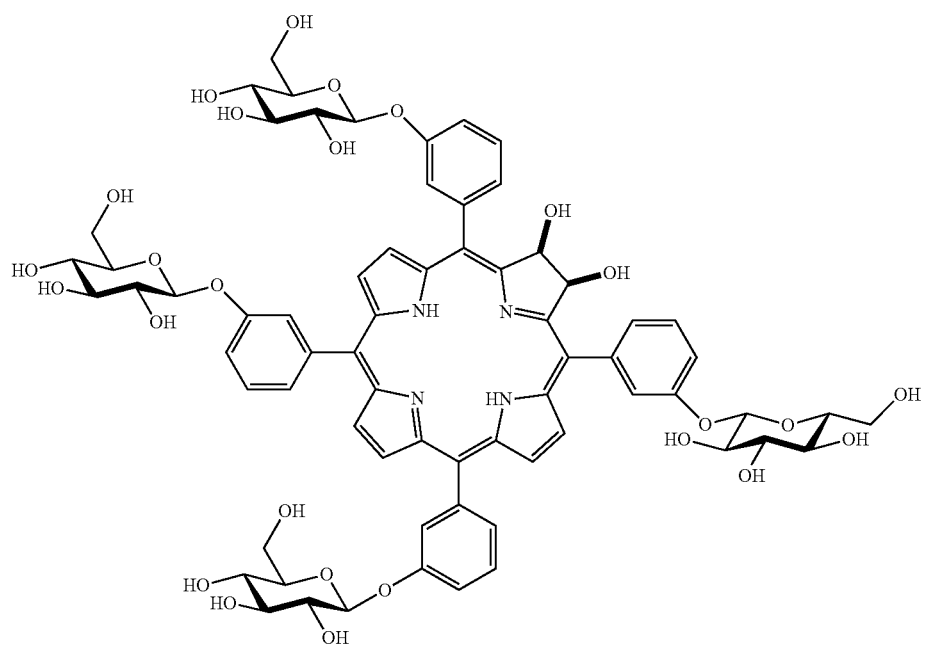

The analytically pure product (55 mg, 77%) was obtained as a violet crystalline solid after recrystallization from dichloromethane/aqueous methanol.

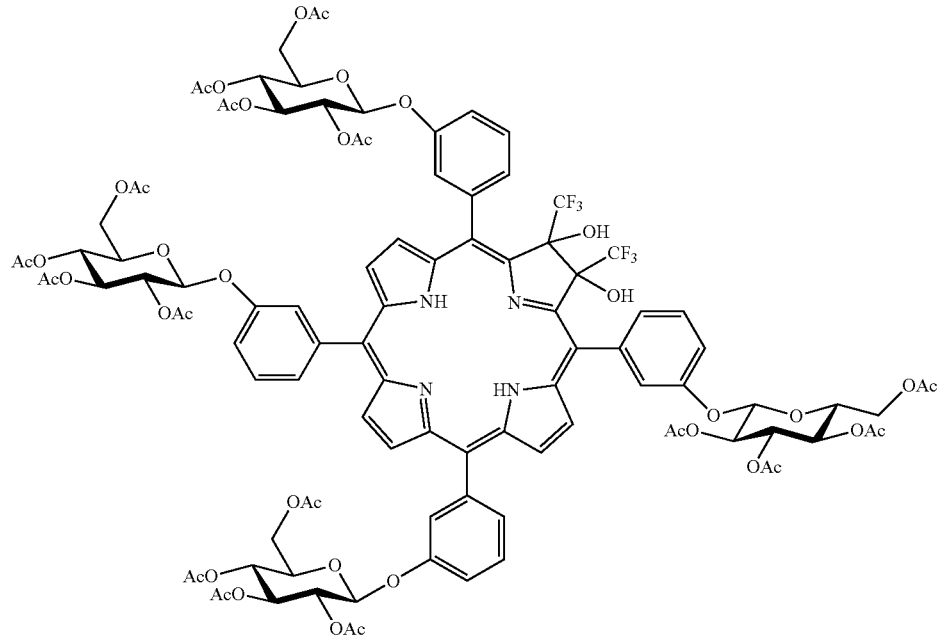

mp: 155° C.; $^1$H-NMR (400 MHz, CDCl$_3$): δ=−1.63−−1.53 (s, 2 H, NH), 0.68-2.16 (m, 48 H, 16×OAc), 3.56-4.33 (m, 14 H, H'ose'), 5.02-5.41 (m, 14 H, H'ose'), 7.34-7.70 (m, 12 H, Ar), 7.83-8.03 (m, 6 H, 2×β-H, 4×Ar), 8.42-8.45 (m, 2 H, β-H), 8.57-8.62 (m, 2 H, β-H) ppm; HRMS (ESI): $C_{102}H_{102}F_6N_4O_{42}Na^+$ ([M+Na]$^+$): required: 2192.5798; found: 2192.5726; UV/Vis (CH$_2$Cl$_2$): λ$_{max}$/nm (ϵ/dm$^3$ mol$^{-1}$ cm$^{-1}$): 408 (167600), 518 (12900), 547 (13000), 599 (5700), 653 (25100).

3.2 Preparation of 5,10,15,20-tetrakis-(3-β-D-glucosylphenyl)-7,8-dihydroxy-7,8-bis-(trifluoromethyl)-7,8-chlorin To a stirred solution of 5,10,15,20-tetrakis-[3-(2,3,4,6-tetraacetyl-β-D-glucosyl)-phenyl]-7,8-dihydroxy-7,8-bis-(trifluoromethyl)-7,8-chlorin (35 mg, 16 μmol) in dry tetrahydrofuran/methanol 1:1 (10 ml) under an argon atmosphere, a solution of sodium methanolate in dry methanol (1.5 ml, 0.1 N) was added. After 15 h, the solvent was evaporated under reduced pressure and the crude product was purified by flash chromatography, using RP$_{18}$ silica gel and methanol/water 9:1 as the eluent. The title product (24 mg, 99%) was obtained as a violet crystalline solid after washing with dichloromethane.

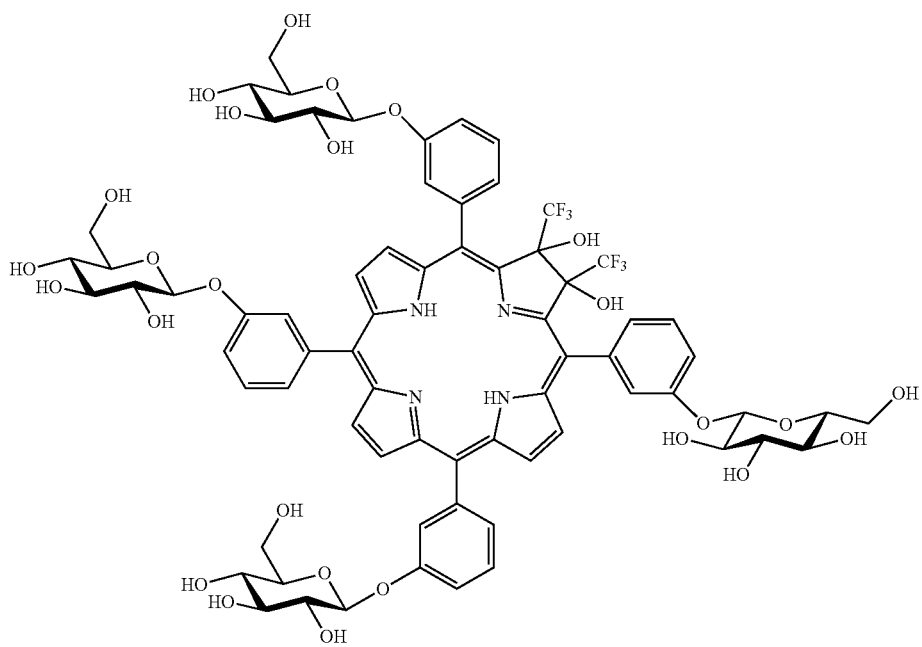

mp: >300° C.; HRMS (ESI): $C_{70}H_{70}F_6N_4O_{26}Na^+$ ([M+Na]$^+$): required: 1519.4075; found: 1519.4110; UV/Vis (EtOH): $\lambda_{max}$/nm ($\epsilon$/dm$^3$ mol$^{-1}$ cm$^{-1}$): 407 (142900), 518 (10400), 547 (10300), 600 (4600), 654 (19200).

Example 4

Photodynamic Inactivation of Bacterial Cell Suspensions

The organisms used in our studies were two members of the microflora wounds; *Staphylococcus aureus* DSM 11729, Gram-positive; and *Pseudomonas aeruginosa* DSM 1117, Gram-negative.

Several studies have demonstrated that Gram-positive bacteria are particularly susceptible to photodynamic inactivation whereas Gram-negative bacteria are significantly more resistant to many commonly used photosensitizers. Moreover, it has been found that Gram-positive and Gram-negative bacterial cells in complex media (e.g. blood, plasma, blood serum, saliva) are much less susceptible to standard photosensitizer conjugates.

Cultures cells are suspended in sterile phosphate-buffered saline (PBS) or sterile PBS supplemented with 10% sterile horse blood serum. The final OD (Optical Density) at 600 nm, 1 cm in all cases was 0.03. The bacterial suspensions are placed into sterile black well plates with clear bottoms. Concentrations of photosensitizer used in the study were as follows: 100 µM, 10 µM and 1 µM.

After an incubation time period of 90 minutes, the samples are exposed to laser light of 652 nm, power set 0.5 W, and irradiation time of 85 s. With the irradiation time, the resulting energy fluency is of about 100 J/cm$^2$. Control plates contained no photosensitizer and are not exposed to laser light. The control samples for dark toxicity are only exposed to photosensitizer without any illumination.

After irradiation, the samples are removed and suspended again in the culture media. The numbers of colony-forming units (CFU/ml) are enumerated after an adequate incubation time period.

Figure 4:
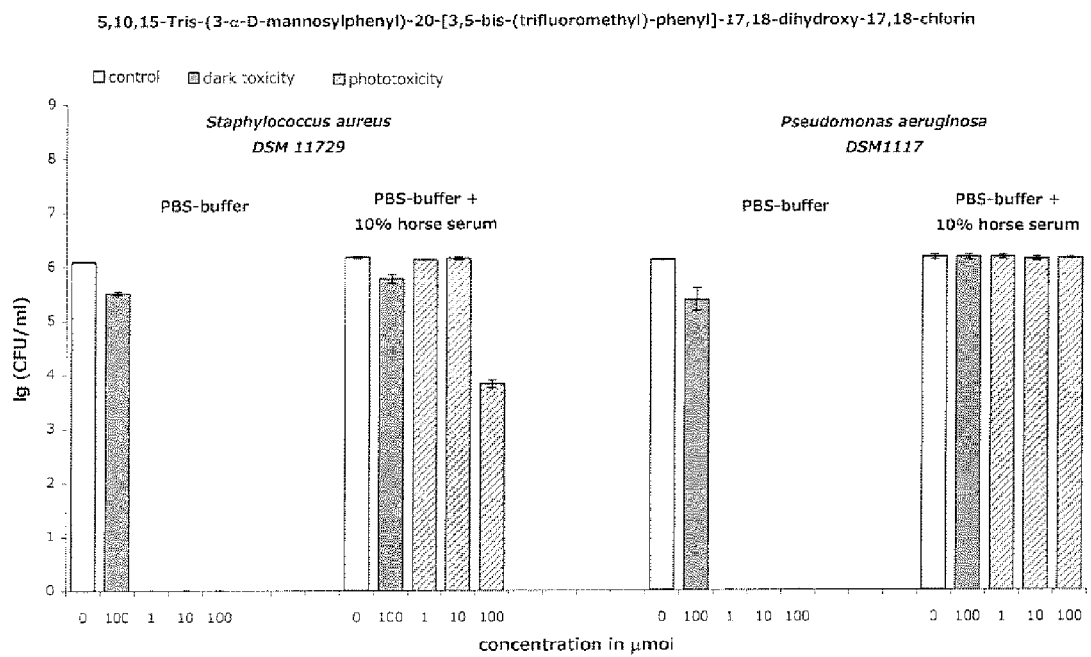
FIG. 4.—shows one embodiment of photodynamic inactivation using 5,10,15-tris-(3-α-D-mannosylphenyl)-20-[3,5-bis-(trifluoromethyl)-phenyl]-17,18-dihydroxy-17,18-chlorin.
Figure 5:
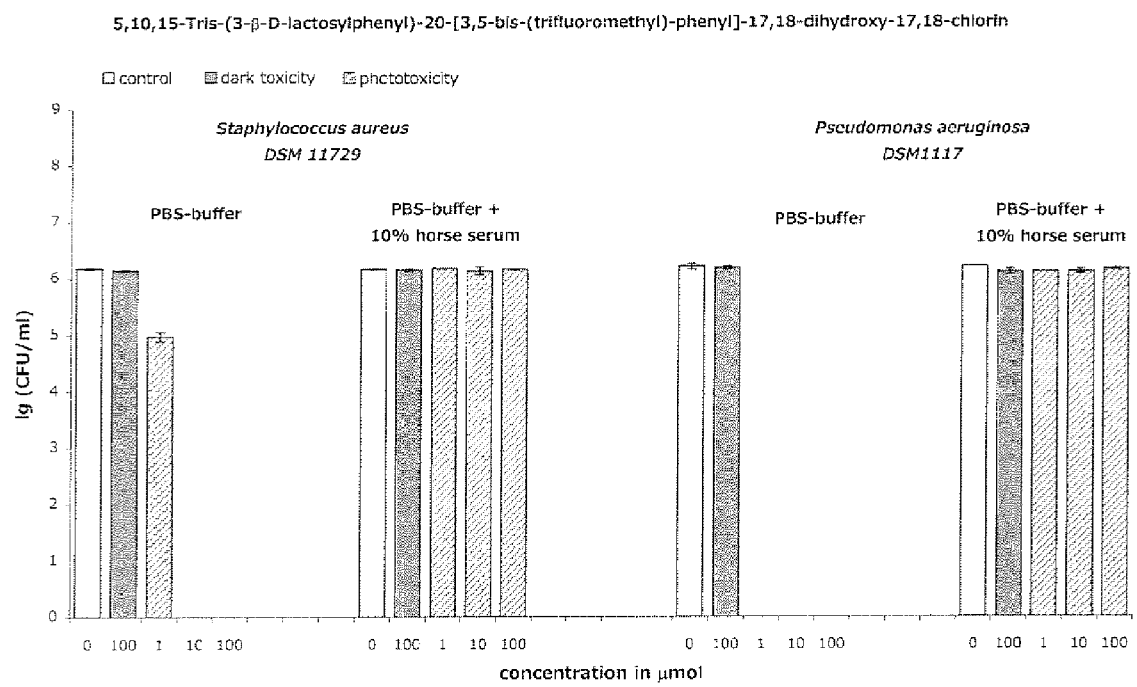
FIG. 5.—shows one embodiment of photodynamic inactivation using 5,10,15-tris-(3-β-D-lactosylphenyl)-20-[3,5-bis-(trifluoromethyl)-phenyl]-17,18-dihydroxy-17,18-chlorin.
Figure 6:
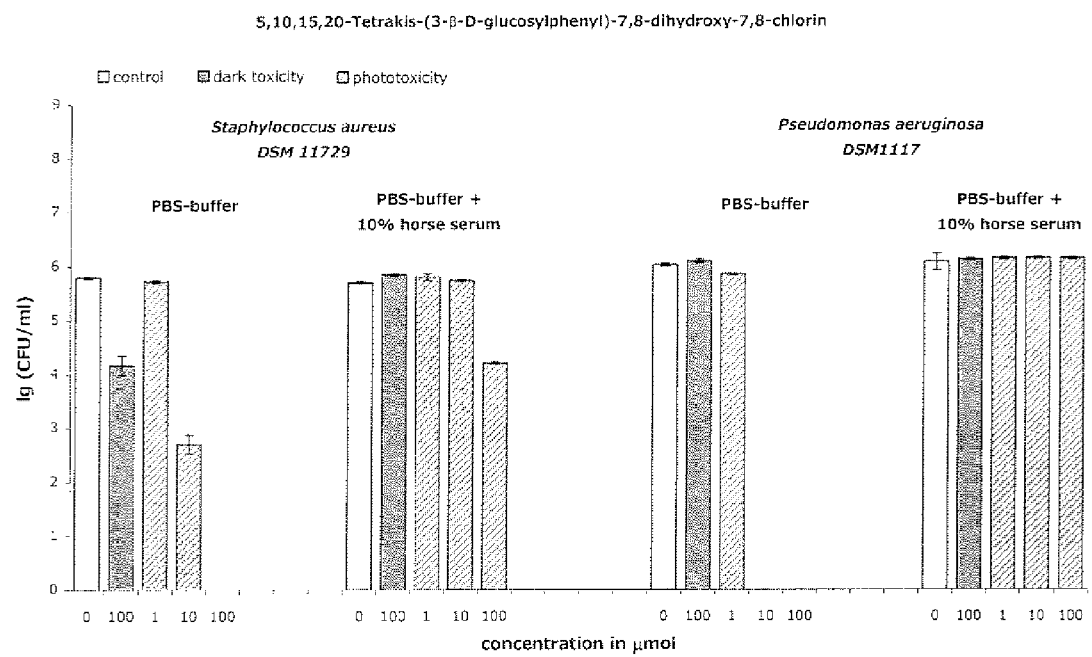
FIG. 6.—shows one embodiment of photodynamic inactivation using 5,10,15,20-tetrakis-(3-β-D-glucosylphenyl)-7,8-dihydroxy-7,8-chlorin.
Figure 7:
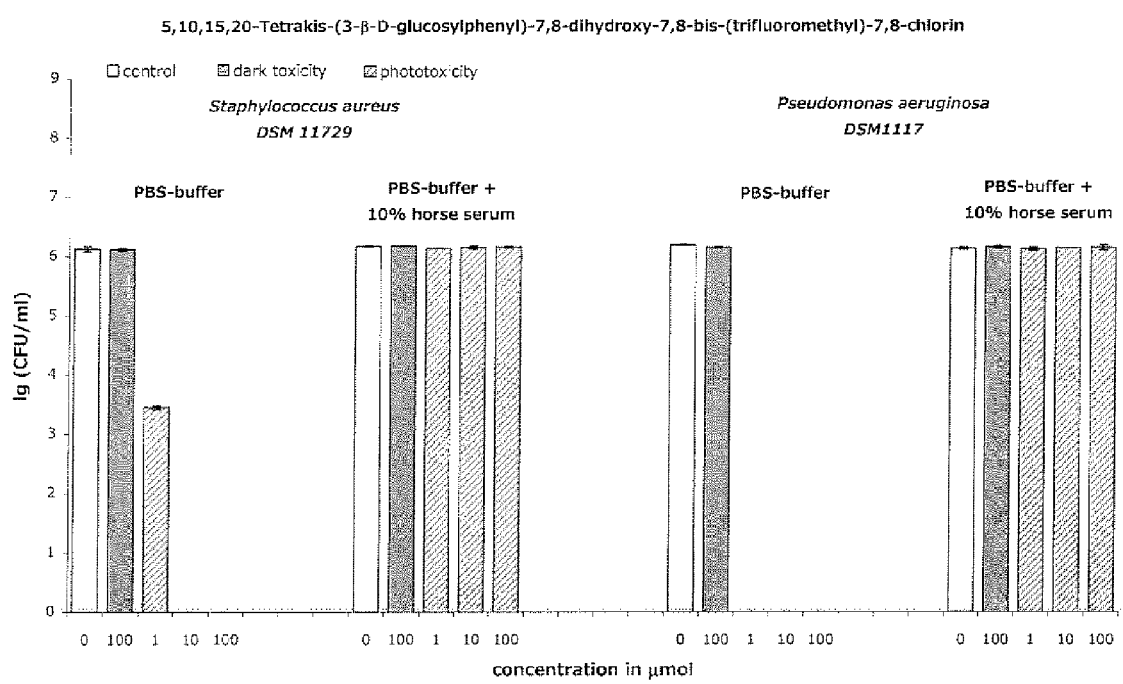
FIG. 7.—shows one embodiment of photodynamic inactivation using 5,10,15,20-tetrakis-(3-β-D-glucosylphenyl)-7,8-dihydroxy-7,8-bis-(trifluoromethyl)-7,8-chlorin.

This example illustrates the photodynamic inactivation of selected photosensitizers against *Staphylococcus aureus* DSM 11729 and *Pseudomonas aeruginosa* DSM 1117 in PBS-buffer and PBS supplemented with 10% sterile horse blood serum. FIG. 1 shows the activity of a porphyrin glycoconjugate and FIGS. 2-7 show the activity of chlorin glycoconjugates.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

What is claimed is:

1. A carbohydrate and dihydroxychlorin conjugate compound comprising formula:

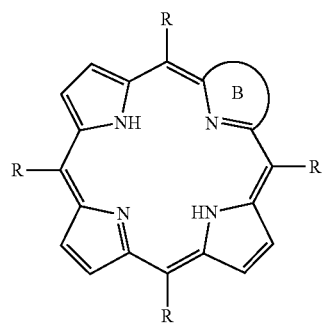

wherein B is independently selected from the group consisting of:

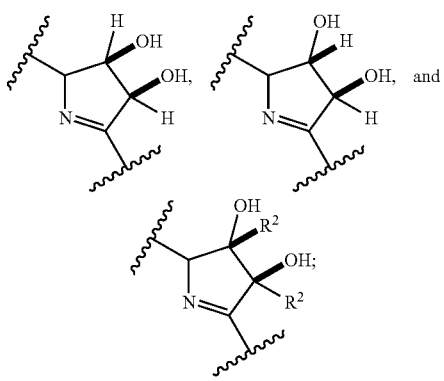

wherein each R is an independently selected substituent comprising one or more carbohydrate groups; and wherein each $R^2$ is independently selected from the group consisting of alkyl or fluoroalkyl groups consisting of 1-15 carbon atoms, a phenyl ring, and a phenyl ring with one or more substituent X;

wherein said substituent X of the phenyl ring is in the ortho-, meta- or para-position of the phenyl ring;

wherein said substituent X is selected from the group consisting of OH, —COOH, —NH$_2$, —CF$_3$, —F, —COOY, —NHY, —OY, —NH—Z—COOH, and —CO—Z—NH$_2$;

wherein Y is selected from the group consisting of a polyethylene glycol residue containing a (CH$_2$CH$_2$O)$_n$ moiety with n=1-30 and a carbohydrate moiety; and wherein Z is selected from the group of peptides and oligopeptides.

2. The compound according to claim 1, based on the formula 3:

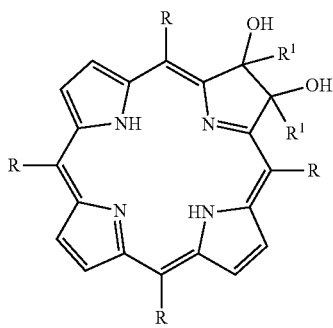

wherein each R comprises one or more carbohydrate groups;

wherein each $R^1$ is independently selected from the group consisting of alkyl or fluoroalkyl groups consisting of 1-15 carbon atoms, a phenyl ring, and a phenyl ring with one or more substituent X;

wherein said substituent X of the phenyl ring is in the ortho-, meta- or para-position of the phenyl ring;

wherein said substituent X is selected from the group consisting of OH, —COOH, —NH$_2$, —F$_3$, —F, —COOY, —NHY, —OY, —NH—Z—COOH, and —CO—Z—NH$_2$;

wherein Y is selected from the group consisting of a polyethylene glycol residue containing a (CH$_2$CH$_2$O)$_n$ moiety with n=1-30 and a carbohydrate moiety; and wherein Z is selected from the group consisting of peptides and oligopeptides.

3. The compound according to claim 2, wherein one or more substituent X is CF$_3$.

4. The compound according to claim 1, based on the formula 1:

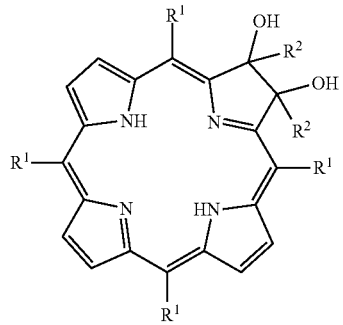

wherein $R^1$ is a phenyl ring with a substituent X;

wherein said substituent X is in the ortho-, meta- or para-position;

wherein said substituent X is selected from the group consisting of a glucosyl, galactosyl, mannosyl, 2-acetamidoglucosyl, lactosyl, cellobiosyl, maltosyl and 3,4,6-trideoxy-3-(dimethylamino)-D-xylo-hexopyranosyl;

wherein each $R^2$ is independently selected from the group consisting of alkyl or fluoroalkyl groups consisting of 1-15 carbon atoms, and a phenyl ring substituted with one or more CF$_3$-groups; and wherein said CF$_3$-groups are in the ortho-, meta- or para-position.

5. The compound according to claim 1, based on the formulas 1 or 2:

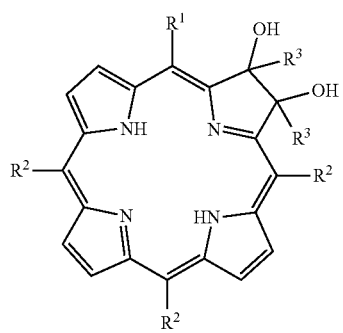

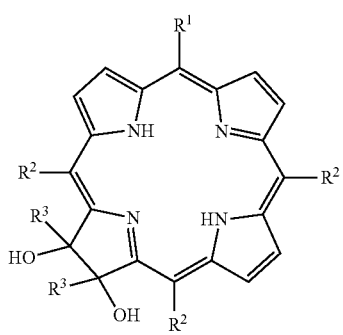

wherein $R^1$ is a phenyl ring with one or more substituent X;

wherein said substituent X is in the ortho-, meta- or para-position;

wherein $R^2$ is a phenyl ring with a substituent X in the ortho-, meta- or para-position;

wherein said substituent X is selected from the group consisting of a glucosyl, galactosyl, mannosyl, 2-acetamidoglucosyl, lactosyl, cellobiosyl, maltosyl and 3,4,6-trideoxy-3-(dimethylamino)-D-xylo-hexopyranosyl;

wherein R³ is selected from the group consisting of alkyl or fluoroalkyl groups consisting of 1-15 carbon atoms, and a phenyl ring substituted with one or more CF₃-groups; and wherein said CF₃-groups are in the ortho-, meta- or para-position.

6. A composition comprising the compound according to claim 1 in an amount which is effective in destroying Gram-negative and Gram-positive microorganisms in the presence of a complex environment selected from the group consisting of saliva, blood, plasma and combinations thereof.

7. The compound according to claim 1 comprising formula:

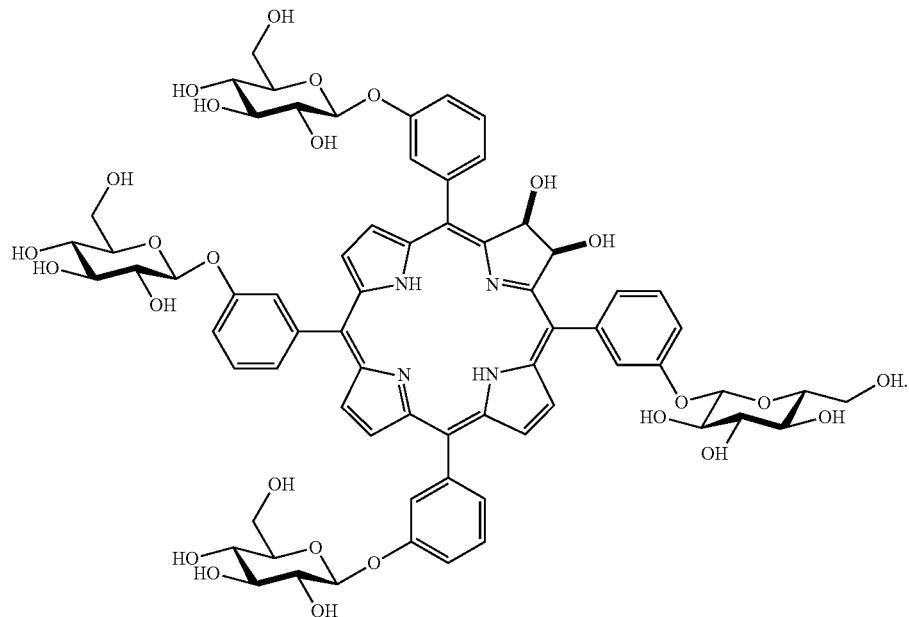

8. The compound according to claim 1 comprising formula:

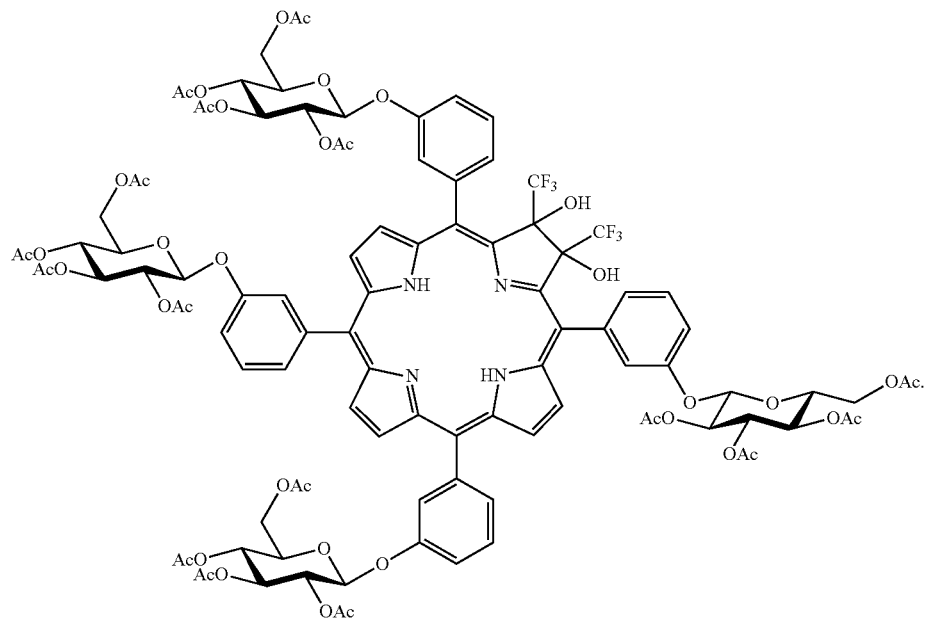

9. The compound according to claim 1 comprising formula:

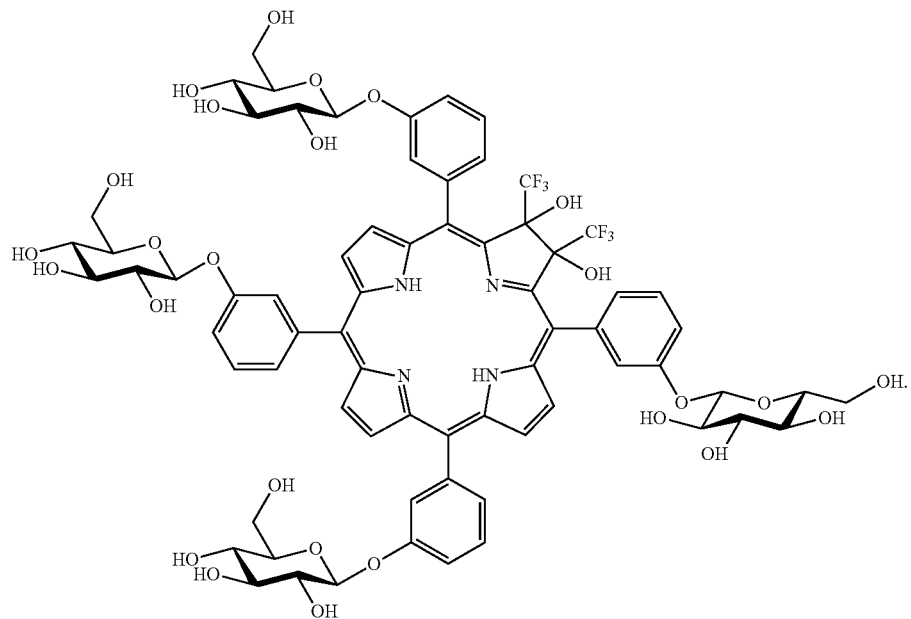

10. The compound according to claim 1, based on the formula 1:

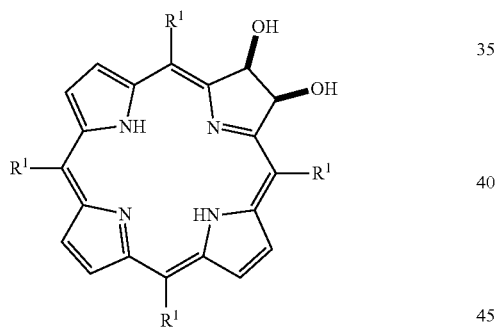

wherein $R^1$ is a phenyl ring with a substituent X;
wherein said substituent X is either in the meta- or para-position;
wherein said substituent X is selected from the group of a glucosyl, galactosyl, mannosyl, 2-acetamidoglucosyl, lactosyl, cellobiosyl, maltosyl, and 3,4,6-trideoxy-3-(dimethylamino)-D-xylo-hexopyranosyl substituent.

* * * * *